United States Patent
Cashman et al.

(10) Patent No.: US 9,023,340 B2
(45) Date of Patent: May 5, 2015

(54) WNT INHIBITORS FOR HUMAN STEM CELL DIFFERENTIATION

(75) Inventors: John Cashman, San Diego, CA (US); Marion Lanier, San Diego, CA (US); Mark Mercola, San Diego, CA (US); Dennis Schade, San Diego, CA (US); Erik Willems, San Diego, CA (US)

(73) Assignee: ChemRegen, Inc., San Diego, CA (US)

( * ) Notice: Subject to any disclaimer, the term of this patent is extended or adjusted under 35 U.S.C. 154(b) by 0 days.

(21) Appl. No.: 13/540,590

(22) Filed: Jul. 2, 2012

(65) Prior Publication Data
US 2013/0177535 A1    Jul. 11, 2013

Related U.S. Application Data

(60) Provisional application No. 61/571,630, filed on Jul. 2, 2011.

(51) Int. Cl.
| | |
|---|---|
| *A01N 63/00* | (2006.01) |
| *C07D 401/12* | (2006.01) |
| *C07D 209/76* | (2006.01) |
| *C12N 5/077* | (2010.01) |
| *A61K 35/34* | (2006.01) |

(52) U.S. Cl.
CPC ............ *C07D 401/12* (2013.01); *C07D 209/76* (2013.01); *C12N 5/0657* (2013.01); *A61K 35/34* (2013.01); *C12N 2501/415* (2013.01); *C12N 2503/02* (2013.01); *C12N 2506/02* (2013.01)

(58) Field of Classification Search
CPC .. C07D 401/12; C07D 209/76; C12N 5/0657; C12N 2501/415; A61K 35/34
USPC ............... 424/93.7; 435/377; 546/169, 276.7; 548/435
See application file for complete search history.

(56) References Cited

FOREIGN PATENT DOCUMENTS

| | | |
|---|---|---|
| WO | WO2009/155001 A2 | 12/2009 |
| WO | WO2009155001 * | 12/2009 |

OTHER PUBLICATIONS

Vippagunta et al, (Adv Drug Deliver Rev, 2001, 48, 3-26).*
Vippagunta et al., Adv. Drug Deliver. Rev., 2001, 48, 3-26.

* cited by examiner

*Primary Examiner* — Jason Sims
*Assistant Examiner* — Ibrahim D Bori

(57) ABSTRACT

Methods and small molecule compounds for stem cell differentiation and treatment of animals with diseases are provided. One example of a class of compounds that may be used is represented by the compound of Formula I and II:

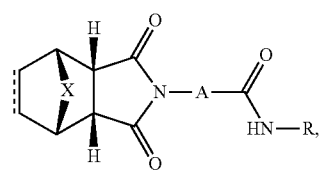

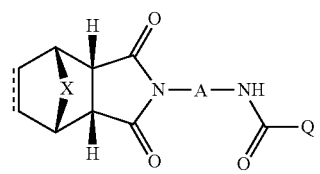

or a pharmaceutically acceptable salt or solvate thereof, wherein A, X, Q, $R_1$, $R_2$, $R_3$, $R_4$ are as described herein.

5 Claims, 2 Drawing Sheets

WNT INHIBITORS FOR HUMAN STEM CELL DIFFERENTIATION

CROSS REFERENCE TO RELATED APPLICATIONS

This application claims the benefit of priority under 35 U.S.C. §119(e) to U.S. Provisional Application No. 61/571,630, titled "WNT INHIBITORS FOR HUMAN STEM CELL DIFFERENTIATION," filed on Jul. 2, 2011, which is hereby incorporated by reference in its entirety for all purposes.

FIELD OF THE INVENTION

The present invention generally relates to the identification of small molecules that cause human stem cell differentiation with applications to the fields of molecular biology and medicine. More specifically, it relates to the discovery of compounds that inhibit the Wnt transduction pathway, including the Wnt beta-catenin pathway, and their use in stem cell differentiation of utility in cardiomyogenesis, cancer and other diseases.

BACKGROUND OF THE DISCLOSURE

Stem cells are a type of cell that could be a source for the replacement of damaged or diseased tissues. Embryonic stem cells (ESCs) are a type of stem cells that are attracting particular interest. The unique characteristics of ESCs include their capacity to regenerate themselves and develop into various cell types of all three embryonic germ layers, i.e., ectoderm, mesoderm and endoderm, under appropriate conditions. Such differentiated cell types include, but are not limited to, muscle, nerve, heart, liver, bone and blood. The potential of ESCs, induced pluripotent stem cells (iPSCs), adult or tissue specific stem cells and the like to grow into specialized cells has attracted interest for research and disease treatment using these cells. The clinical application of stem cells involves harvesting of these cells and transplantation of the cells into individuals with failing organs in order to restore the function of the organs with or without prior in vitro differentiation. Another application involves differentiating large quantities of stem cells into particular human cell types in a biotechnology sense and using these cells for pharmaceutical drug testing or toxicity testing.

Emerging evidence suggests that the Wnt signaling pathway regulates crucial aspects of cardiac morphogenesis and self-renewal and differentiation of cardiac progenitor cells. Stem cell differentiation is a complex process that appears to have a temporal role in cardiovascular development as shown by Keller and Yang (Yang et al., Nature, 2008, 453, p. 524-528). The activity of the Wnt/β-catenin signaling pathway is dependent on the amount of β-catenin in the cytoplasm. Normally, cytoplasmic β-catenin is maintained at a low level through degradation that is regulated by a multiprotein "destruction" complex containing Axin. Upon Wnt stimulation, Axin translocates to the cell membrane to interact with LRP5 and Dvl. Dvl becomes phosphorylated and subsequently inhibits GSK3β phosphorylation of β-catenin thereby resulting in the accumulation of non-phosphorylated β-catenin in the cytoplasm. Non-phosphorylated β-catenin avoids degradation and translocates into the nucleus. Upon entering the nucleus, β-catenin binds to the transcription factors Tcf/LEF that promotes the expression of Tcf-regulated genes. Binding to Tcf/LEF is enabled by the presence of coactivators (CBP and/or P300). Accordingly, identification of compounds and methods for modulating and/or inhibiting Wnt pathways may offer an avenue for stem cell differentiation including the production of cardiomyocytes and for the therapeutic treatment of diseases including cancer and other proliferative diseases associated with this pathway.

SUMMARY OF THE INVENTION

The present invention provides compounds and their use as Wnt signaling inhibitors. Also provided are methods of synthesis of these compounds and pharmaceutical compositions thereof.

In one aspect, the present invention provides a method of inhibiting Wnt signaling in a cell comprising administering to the cell an effective amount of a compound of Formula I:

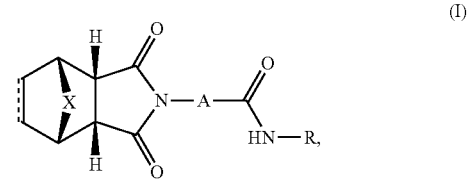

or a pharmaceutically acceptable salt or solvate thereof, wherein:
A is phenyl or cis-cyclohexyl or trans-cyclohexyl substituted in a 1,4-pattern and optionally substituted;
X is $CH_2$, $CH_2$—$CH_2$, or heteroatoms (O, S, N);
R is:

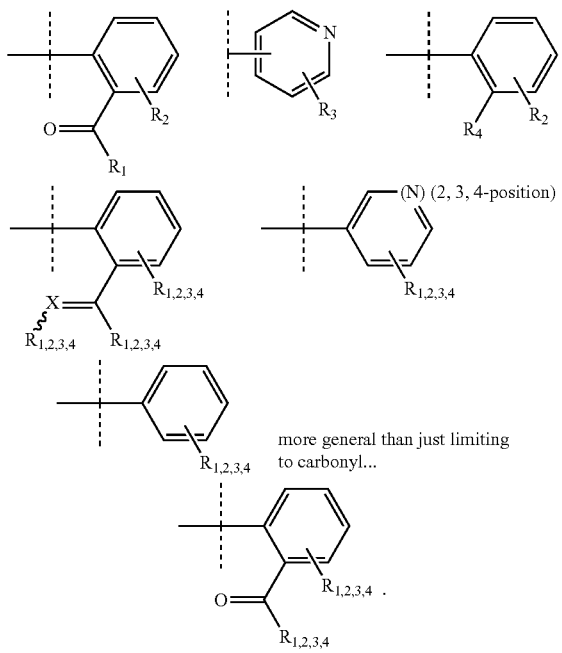

R1 is a $C_{1-4}$ alkyl, $C_{1-4}$ alkoxy, substituted $C_{1-4}$ alkyl, substituted $C_{1-4}$ alkoxy, $C_{1-4}$ alkyl amine, $C_{2-6}$ cyclic amine, aryl, heteroaryl;
R2 is hydrogen, $C_{1-4}$ alkyl, $C_{1-4}$ alkoxy, substituted $C_{1-4}$ alkyl, substituted $C_{1-4}$ alkoxy, $C_{1-4}$ alkyl amine, heteroalkyl, halogens, fluorinated alkyl;
R3 is selected from the groups consisting of hydrogen, halogen, $C_{1-4}$ alkyl, $C_{1-4}$ alkoxy, substituted $C_{1-4}$ alkyl, substituted C$_{1-4}$ alkoxy, hydroxyl, trifluoromethyl, acyl-C$_{1-4}$alkyl, C$_{1-4}$ alkyl amine, C$_{2-6}$ cyclic amine, C$_{1-4}$ ester, C$_{1-4}$ amide, heteroaryl;

R4 is a heteroaryl such as but not limited to furan, oxazole, pyrazole,

R1 and R2 can be joined to form a ring or can be comprised of the following moiety:

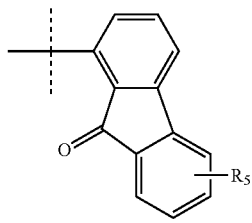

R5 is a hydrogen, halogen, C$_{1-4}$ alkyl, C$_{1-4}$ alkoxy, substituted C$_{1-4}$ alkyl, substituted C$_{1-4}$ alkoxy;

=== is either a double or a single bond.

In one aspect, the present invention provides a method of inhibiting Wnt signaling in a cell comprising administering to the cell an effective amount of a compound of Formula II:

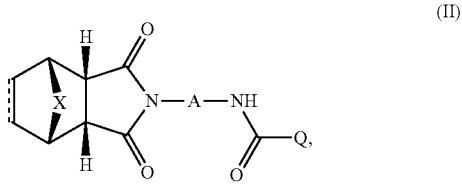

(II)

or a pharmaceutically acceptable salt or solvate thereof, wherein:

A is phenyl or cis-cyclohexyl or trans-cyclohexyl substituted in a 1,4-pattern and optionally substituted;

X is CH$_2$, CH$_2$—CH$_2$, oxygen;

Q is aryl, quinoline, isoquinoline,

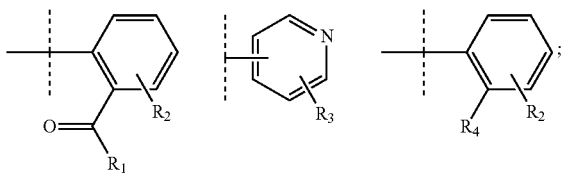

R1 is a C$_{1-4}$ alkyl, C$_{1-4}$ alkoxy, substituted C$_{1-4}$ alkyl, substituted C$_{1-4}$ alkoxy, C$_{1-4}$ alkyl amine, C$_{2-6}$ cyclic amine, aryl, heteroaryl;

R2 is hydrogen, C$_{1-4}$ alkyl, C$_{1-4}$ alkoxy, substituted C$_{1-4}$ alkyl, substituted C$_{1-4}$ alkoxy, C$_{1-4}$ alkyl amine, heteroalkyl, halogens, fluorinated alkyl;

R3 is selected from the groups consisting of hydrogen, halogen, C$_{1-4}$ alkyl, C$_{1-4}$ alkoxy, substituted C$_{1-4}$ alkyl, substituted C$_{1-4}$ alkoxy, hydroxyl, trifluoromethyl, acyl-C$_{1-4}$alkyl, C$_{1-4}$ alkyl amine, C$_{2-6}$ cyclic amine, C$_{1-4}$ ester, C$_{1-4}$ amide, heteroaryl;

R4 is a heteroaryl such as but not limited to furan, oxazole, pyrazole;

R1 and R2 can be joined to form a ring or the following moiety

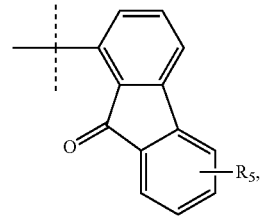

R5 is a hydrogen, halogen, C$_{1-4}$ alkyl, C$_{1-4}$ alkoxy, substituted C$_{1-4}$ alkyl, substituted C$_{1-4}$ alkoxy; and === is either a double or a single bond.

In another aspect the disclosure provides methods for stem cell differentiation, comprising contacting embryonic stem cells with a compound of structures I and II in the form of a free base or a pharmaceutically acceptable salt, hydrate, solvate or N-oxide thereof, wherein A, X, Q, R$_1$, R$_2$, R$_3$, R$_4$ are as described above.

DETAILED DESCRIPTION OF THE EMBODIMENTS

Figure 1:
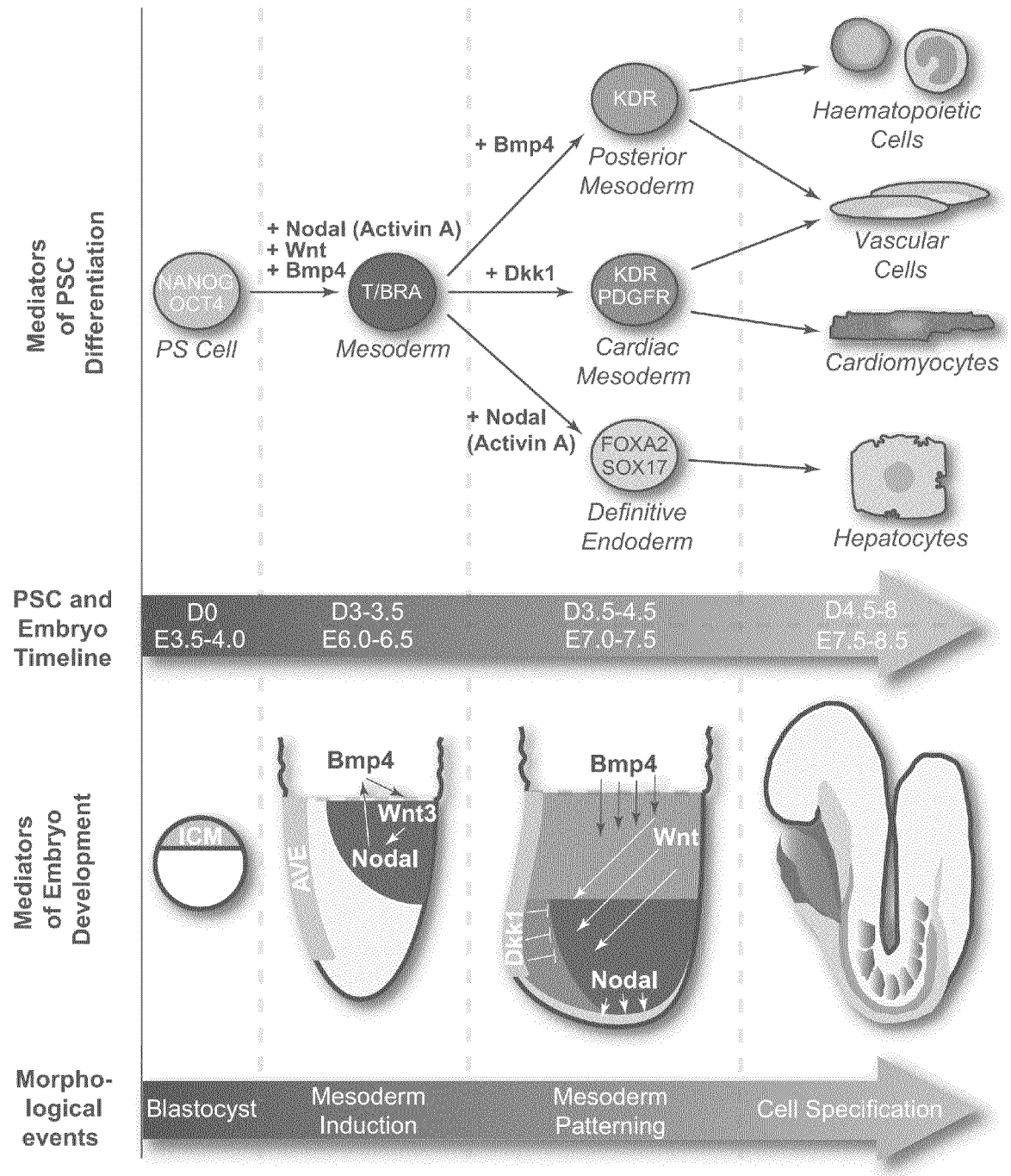
FIG. 1 shows a schematic comparison of heart induction in embryos and ESCs (both small animal and human). A small number of biological factors can efficiently drive differentiation in Plurippotent Stem Cells (upper panel) in an apparent recapitulation of the processes that direct heart development in the embryo (lower panel). Nodal, Wnt and BMP induce cardiogenic mesoderm, but need to be blocked in order for cardiac development to proceed, constraining heart development to a region of anterior endoderm in the late gastrula stage embryo (lower, middle) (Willems, E., Mercola, M. Cell Stem Cell. 2011; 8:124-126).
Figure 2:
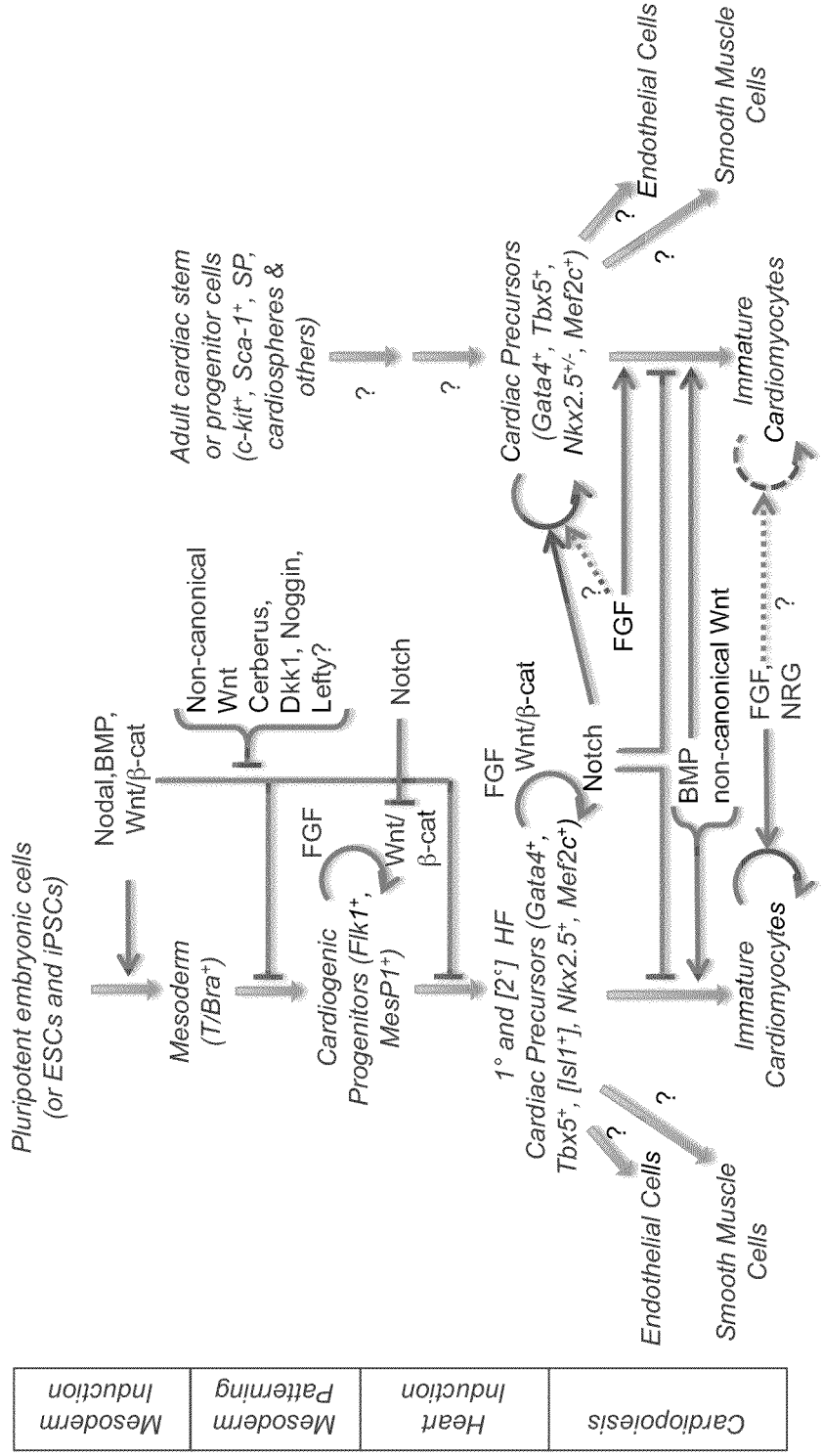
FIG. 2 provides a summary model for signaling pathways in cardiomyocyte formation. Extracellular signaling molecules positively (green) and negatively (red) control mesoderm induction to cardiopoietic differentiation in the embryo. Adult cardiac precursors share genetic markers with their developmental counterparts, but developmental signals also control regeneration, suggesting parallels between development and the control of adult cardiomyocyte renewal (Mercola et al. Genes Dev. 2011; 25:299-309).

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The term "lipophilic" refers to moieties having an affinity for lipids and other fat-like substances, tending to combine with, and capable of partitioning into them.

The term "cardiomyocytes" refers to cells of muscular tissue in the heart.

The term "embryonic stem cell" refers to cell from the inner group of cells of an early embryo (blastocyst), with the potential to become most or all of the body tissues.

The term "stem cell differentiation" refers to a series of events involved in the development of specialized cells from stem cells, where the specialized cells have specific structural, functional, and biochemical properties.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—, —CH$_2$CH═CHCH$_2$—, —CH$_2$CCCH$_2$—, —CH$_2$CH$_2$CH(CH$_2$CH$_2$CH$_3$)CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH— O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S— CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O) OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom.

The term "oxo" as used herein means an oxygen atom that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms, for example, nitrogen, sulfur or oxygen within the ring.

The term "methylthio" refers to a moiety —S—$CH_3$.

The terms "furyl," "tetrahydrofuryl," and "pyridyl" refer to radicals formed by removing one hydrogen from the molecules of furan, tetrahydrofuran, and pyridine, respectively.

The terms "alkyl amine" and "cyclic amine" refer to alkanes or cycloalkanes, respectively, having one hydrogen substituted by a primary, secondary or tertiary amino group, as well as to the moieties and radicals derived from such amines.

The term "alkyl amide" by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons), which is attached to a nitrogen atom, which may be a secondary or tertiary amino group, attached to a carbonyl (C=O) group, e.g., ($C_1$-$C_{10}$) NHC(=O)— and ($C_1$-$C_{10}$)$_2$NC(=O)—.

The term "alkyl amide" refers to, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO2R', —C(O)NR'R", —OC(O)NR'R", —NR"C(O)R', —NR'—C(O)NR"R"', —NR"C(O)OR', —NR—C(NR'R")=NR"', —S(O)R', —S(O)$_2$R', —S(O)2NR'R", —NRSO$_2$R', —CN and —NO$_2$ in a number ranging from zero to (2m'+1), where m' is the total number of carbon atoms in such radical. R', R", R"' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2$ $CF_3$) and acyl (e.g., —C(O)$CH_3$, —C(O) $CF_3$, —C(O)$CH_2$O $CH_3$, and the like).

The term "alkoxy" refers to the moiety —O-alkyl, wherein alkyl is as defined above. Examples of alkoxy structures that are within the purview of the definition include, but are not limited to, ($C_1$-$C_6$)alkoxy radicals, such as methoxy, ethoxy, propoxy, isopropoxy, butoxy, iso-butoxy, sec-butoxy, tert-butoxy, pentoxy, 3-pentoxy, or hexyloxy.

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO2R', —C(O)NR'R", —OC(O)NR'R", —NR"C(O)R', —NR'—C(O)NR"R"', —NR"C(O)OR', —NR—C (NR'R"R"')=NR", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R"' and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C (O)—(CRR')q-U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-($CH_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'— (C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the disclosure may exist as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When the disclosed compounds contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)-or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

∼∼∼ describes a bond of any stereochemistry.

The term "tautomer," as used herein, refers to one of two or more structural isomers which exist in equilibrium and which are readily converted from one isomeric form to another. It will be apparent to one skilled in the art that certain compounds of the disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures with the exception of the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the disclosure, whether radioactive or not, are encompassed within the scope of the disclosure.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

The description of compounds of the disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The disclosure also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the disclosure.

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as -toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The pharmaceutical compositions for the administration of the compounds of this embodiment either alone or in combination with other agents, e.g., chemotherapeutic, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, poly-vinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, para-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agent.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether β-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the disclosure are employed. For purposes of this application, topical application shall include mouthwashes and gargles.

In the methods described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or once or twice per day. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one embodiment the disclosure provides a compound of Formula I:

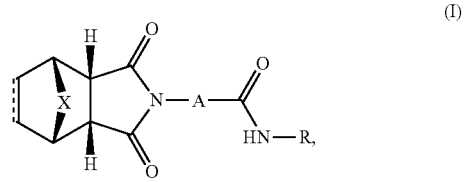

or a pharmaceutically acceptable salt or solvate thereof, wherein:

A is phenyl or cis-cyclohexyl or trans-cyclohexyl substituted in a 1,4-pattern and optionally substituted;

X is $CH_2$, $CH_2$—$CH_2$, oxygen;

R is:

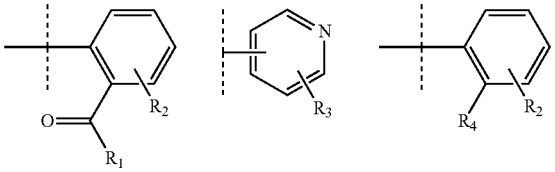

R1 is a $C_{1-4}$ alkyl, $C_{1-4}$ alkoxy, substituted $C_{1-4}$ alkyl, substituted $C_{1-4}$ alkoxy, $C_{1-4}$ alkyl amine, $C_{2-6}$ cyclic amine, aryl, heteroaryl;

R2 is hydrogen, $C_{1-4}$ alkyl, $C_{1-4}$ alkoxy, substituted $C_{1-4}$ alkyl, substituted $C_{1-4}$ alkoxy, $C_{1-4}$ alkyl amine, heteroalkyl, halogens, fluorinated alkyl;

R3 is selected from the groups consisting of hydrogen, halogen, $C_{1-4}$ alkyl, $C_{1-4}$ alkoxy, substituted $C_{1-4}$ alkyl, substituted $C_{1-4}$ alkoxy, hydroxyl, trifluoromethyl, acyl-$C_{1-4}$alkyl, $C_{1-4}$ alkyl amine, $C_{2-6}$ cyclic amine, $C_{1-4}$ ester, $C_{1-4}$ amide, heteroaryl;

R4 is a heteroaryl such as but not limited to furan, oxazole, pyrazole;

R1 and R2 can be joined to form a ring or can be comprised of the following moiety

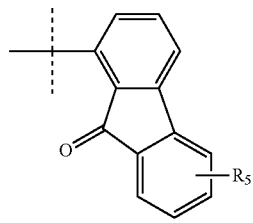

R5 is a hydrogen, halogen, $C_{1-4}$ alkyl, $C_{1-4}$ alkoxy, substituted $C_{1-4}$ alkyl, substituted $C_{1-4}$ alkoxy;

=== is either a double or a single bond.

In another aspect the disclosure provides a compound of Formula IB:

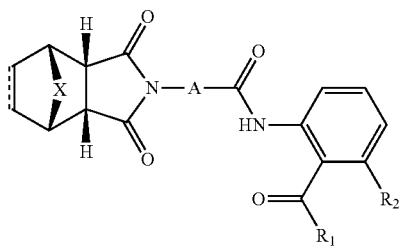

(IB)

or a pharmaceutically acceptable salt or solvate thereof, wherein:

A is phenyl or cis-cyclohexyl or trans-cyclohexyl substituted in a 1,4-pattern and optionally substituted;

X is $CH_2$, $CH_2$—$CH_2$, oxygen;

R1 is a $C_{1-4}$ alkyl, $C_{1-4}$ alkoxy, substituted $C_{1-4}$ alkyl, substituted $C_{1-4}$ alkoxy, $C_{1-4}$ alkyl amine, $C_{2-6}$ cyclic amine, aryl, heteroaryl;

R2 is hydrogen, $C_{1-4}$ alkyl, $C_{1-4}$ alkoxy, substituted $C_{1-4}$ alkyl, substituted $C_{1-4}$ alkoxy, $C_{1-4}$ alkyl amine, heteroalkyl, halogens, fluorinated alkyl;

R1 and R2 can be joined to form a ring or can be comprised of the following moiety

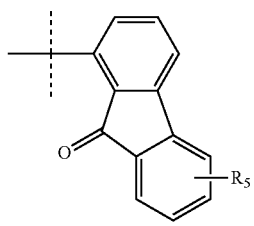

R5 is a hydrogen, halogen, $C_{1-4}$ alkyl, $C_{1-4}$ alkoxy, substituted $C_{1-4}$ alkyl, substituted $C_{1-4}$ alkoxy;

=== is either a double or a single bond.

In another aspect the disclosure provides a compound of Formula IC,

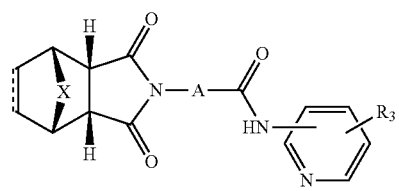

(IC)

A is phenyl or cis-cyclohexyl or trans-cyclohexyl substituted in a 1,4-pattern and optionally substituted, X is $CH_2$, $CH_2$—$CH_2$, oxygen; R3 is selected from the groups consisting of hydrogen, halogen, $C_{1-4}$ alkyl, $C_{1-4}$ alkoxy, substituted $C_{1-4}$ alkyl, substituted $C_{1-4}$ alkoxy, hydroxyl, trifluoromethyl, acyl-$C_{1-4}$alkyl, $C_{1-4}$ alkyl amine, $C_{2-6}$ cyclic amine, $C_{1-4}$ ester, $C_{1-4}$ amide, heteroaryl;

=== is either a double or a single bond.

In another aspect, the present invention provides a method of inhibiting Wnt signaling in a cell comprising administering to the cell an effective amount of a compound of Formula II:

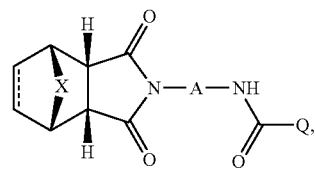

(II)

or a pharmaceutically acceptable salt or solvate thereof, wherein:

A is phenyl or cis-cyclohexyl or trans-cyclohexyl substituted in a 1,4-pattern and optionally substituted;

X is $CH_2$—$CH_2$, oxygen;

Q is aryl, quinoline, isoquinoline,

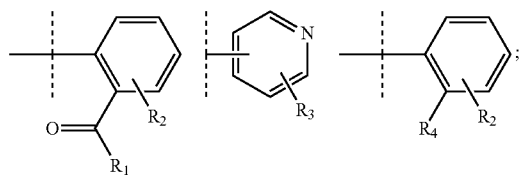

R1 is a $C_{1-4}$ alkyl, $C_{1-4}$ alkoxy, substituted $C_{1-4}$ alkyl, substituted $C_{1-4}$ alkoxy, $C_{1-4}$ alkyl amine, $C_{2-6}$ cyclic amine, aryl, heteroaryl;

R2 is hydrogen, $C_{1-4}$ alkyl, $C_{1-4}$ alkoxy, substituted $C_{1-4}$ alkyl, substituted $C_{1-4}$ alkoxy, $C_{1-4}$ alkyl amine, heteroalkyl, halogens, fluorinated alkyl;

R3 is selected from the groups consisting of hydrogen, halogen, $C_{1-4}$ alkyl, $C_{1-4}$ alkoxy, substituted $C_{1-4}$ alkyl, substituted $C_{1-4}$ alkoxy, hydroxyl, trifluoromethyl, acyl-$C_{1-4}$alkyl, $C_{1-4}$ alkyl amine, $C_{2-6}$ cyclic amine, $C_{1-4}$ ester, $C_{1-4}$ amide, heteroaryl;

R4 is a heteroaryl such as but not limited to furan, oxazole, pyrazole;

R1 and R2 can be joined to form a ring or the following moiety

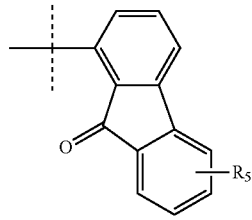

R5 is a hydrogen, halogen, $C_{1-4}$ alkyl, $C_{1-4}$ alkoxy, substituted $C_{1-4}$ alkyl, substituted $C_{1-4}$ alkoxy;

=== is either a double or a single bond.

Some specific norbornene-based compounds within structures I and II include, but are not limited to, compounds 1-22.

In another aspect the disclosure provides methods for producing differentiated cells from stem cells by contacting the stem cells with a compound of Formula I or II.

In another aspect the disclosure provides methods for treating or preventing a cardiac disease or condition in a subject in need thereof, by contacting a cell capable of differentiating into a cardiomyocyte cell with a compound of Formula I or a compound of Formula II; and transplanting the differentiated cardiomyocyte cell into the cardiac tissue of the subject.

In another aspect the disclosure provides methods for producing differentiated cells from stem cells by contacting the stem cells with a compound of Formula I or II, wherein contacting the stem cells with a compound of Formula I or II is from about 24 hours to about 192 hours.

In another aspect the disclosure provides methods for producing differentiated cells from stem cells by contacting the stem cells with a compound of Formula I or II. The differentiated derivatives can be cardiomyocytes, hepatocytes, blood cells, vascular cells, neural or neuronal cells, pancreatic islet cells, or any other cell type induced by Wnt inhibition.

In another aspect the disclosure provides methods for producing differentiated cells from stem cells by contacting the stem cells with a compound of Formula I or II and also further contacting the cells with Activin A.

In another aspect the disclosure provides methods for producing differentiated cells from stem cells by contacting the stem cells with a compound of Formula I or II, wherein the cells differentiate to cardiac mesoderm.

In another aspect the disclosure provides methods for producing differentiated cells from stem cells by contacting the stem cells with a compound of Formula I or II, further comprising contacting the cells with a Wnt protein.

In another aspect the disclosure provides methods for producing differentiated cells from stem cells by contacting the stem cells with a compound of Formula I or II, further comprising contacting the cells with a Wnt protein, wherein the Wnt protein is Wnt3a. In other aspects the Wnt protein is Wnt5a or Wnt7.

In another aspect the disclosure provides methods for producing differentiated cells from stem cells by contacting the stem cells with a compound of Formula I or II, wherein the stem cells are embryonic stem cells, induced pluripotent stem cells or adult stem cells.

In another aspect the disclosure provides methods for stem cell differentiation, comprising contacting the embryonic stem cells with a compound of structure I or II, in the form of free base or a pharmaceutically acceptable salt, hydrate, solvate or N-oxide thereof.

Those skilled in the art may determine the optimal time of contacting the stem cells and with the disclosed compounds described below required achieving the optimal results. As a guideline, the period of contact may be between about 24 hours and about 192 hours, for example. Differentiated cells produced by the disclosed methods may include are cardiomyocytes, liver cells, lung cells, pancreatic cells, and others.

The stem cells suitable for use in the disclosed methods may be derived from a patient's own tissue. This would enhance compatibility of differentiated tissue grafts derived from the stem cells with the patient. In this context it should be noted that embryonic stem cells can include adult stem cells derived from a person's own tissue iPSCs, embryonic stem cells, and the like. Human stem cells may be genetically modified prior to use through introduction of genes that may control their state of differentiation prior to, during or after their exposure to embryonic cell or extracellular medium from an embryonic cell. They may be genetically modified through introduction of vectors expressing a selectable marker under the control of a stem cell specific promoter, such as Oct-4. The stem cells may be genetically modified at any stage with a marker so that the marker is carried through to any stage of cultivation. The marker may be used to purify the differentiated or undifferentiated stem cell populations at any stage of cultivation.

The disclosure also provides differentiated cells produced according to the disclosed methods that may be used for transplantation, cell therapy or gene therapy. The disclosure further provides a differentiated cell produced according to the disclosed methods that may be used for therapeutic purposes, such as in methods of restoring cardiac function in a subject suffering from a heart disease or condition.

In another aspect the disclosure provides methods of treating or preventing a cardiac disease or condition, the method including introducing an isolated differentiated cardiomyocyte cell of the disclosure and/or a cell capable of differentiating into a cardiomyocyte cell when treated in accordance with the disclosed methods into cardiac tissue of a subject. The isolated cardiomyocyte cell may be transplanted into damaged cardiac tissue of a subject. The method may result in the restoration of cardiac function in a subject.

In another aspect the disclosure provides methods of repairing cardiac tissue, the method including introducing an isolated cardiomyocyte cell of the disclosure and/or a cell capable of differentiating into a cardiomyocyte cell when treated in accordance with the method of the disclosure into damaged cardiac tissue of a subject.

The subject may be suffering from a cardiac disease or condition. In the method of the disclosure, the isolated cardiomyocyte cell may be transplanted into damaged cardiac tissue of a subject. The method may result in the restoration of cardiac function in a subject. The disclosure also provides a myocardial model for testing the ability of stem cells that have differentiated into cardiomyocytes to restore cardiac function. The disclosure further provides a cell composition including a differentiated cell of the disclosure, and a carrier.

The term "inducing differentiation" as used herein is taken to mean causing a stem cell to develop into a specific differentiated cell type as a result of a direct or intentional influence on the stem cell. Influencing factors in addition to the compounds described herein can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density.

In another aspect the disclosure provides methods for producing cardiomyocyte cells with acceptable yields. The method may result in the production of cardiomyocytes for in vitro testing for screening purposes, drug development, toxicity testing or clinical application.

SCs and the cell providing the differentiating factor(s) may be co-cultured in vitro. This typically involves introducing the stem cell to an embryonic cell monolayer produced by proliferation of the embryonic cell in culture.

The cellular and molecular events regulating the induction and tissue-specific differentiation of endoderm are important to understanding the development and function of many organ systems. Stem cell-derived endoderm is important for the development of cellular therapies for the treatment of disease such as diabetes, liver cirrhosis, or pulmonary emphysema (e.g., via development of islet cells, hepatocytes or lung cells, respectively). Accordingly, compounds described in the disclosure find particular use in inducing differentiation of cells in the endoderm lineage, including pancreas, liver, lung and the like.

In one aspect, the compounds of this disclosure are used to screen for targets of their action. For example, competitive analyses can be performed using compounds with known targets. Such targets include, for example, but not limited to MEF2C; Beta-catenin; TCF/LEF; Smad2, Smad3; Smad4 (binding partners of the above proteins are also potential targets because they would modulate activity); p38, and components of the signaling that activate MEF2C; components of the Wnt pathway, such as Frizzled proteins, CaMK, Axin, Dishevelled, APC, GSK3, FRAP; Calmodulin; Potassium channel targets; and Calcium channel targets.

In one aspect, the compounds of this disclosure are used as drugs to treat patients in order to boost their endogenous regeneration.

EXAMPLES

The embodiments of the disclosure may be further illustrated by the following non-limiting examples.

Example 1

Biological Assays

Wnt assay protocol: 293T cells were grown in DMEM-high glucose (phenol red) supplemented with 10% (v/v) FBS and 1 mM L-glutamine. 1 million (M) cells were transfected with 1 µg Super(7×)TOPflash (Addgene plasmid 12456: M50 Super 8× TOPflash; 1 µg Wnt3a)—and 0.1 µg TK-Renilla-Lux (pRL-TK vector)-vectors using lipofectamine 2000 reagent according to the manufacturer's protocol. Cells were allowed to adhere for 8-10 hours, lifted with trypsin/EDTA, centrifuged, homogenized and counted before seeding 25,000 cells/well onto 96-well plates. After letting cells settle and attach for 1-2 hours in the incubator, a dose of test compound (and media/DMSO controls) was added. Plates were incubated for 18-20 hours and luciferase activities were determined using a Dual-Luciferase assay kit according to the manufacturer's instructions. Chemiluminescence was recorder on a plate reader instrument, and firefly-derived luminescence was normalized against renilla luminescence. Data were derived from at least two independent experiments, with a minimum of three replicates per condition. Non-linear regression analysis (log dose/response) was done using Prism 5 software.

Human embryonic stem cell culture high content screening assay

Human embryonic stem cell (hESC) H9 lines carrying MYH6-mCherry reporters were maintained: in brief, cells were grown on a mouse embryonic fibroblast coated matrigel plate in Knock Out DMEM media supplemented with 20% Knock Out Serum Replacement and 8 ng/ml bFGF. For embryoid body (EB) differentiation, hESC were mechanically passaged onto gelatin-coated dishes preseeded with mouse embryonic fibroblasts. After 4 days hESC colonies were lifted off with a 10 minute 1 mg/ml collagenase IV treatment and directly differentiated in StemPro 34 with addition of 0.5 ng/ml Bmp4 from day 0-1, 10 ng/ml Bmp4, 5 ng/ml bFGF and 3 ng/ml Activin A from day 1-4. At day 4 and were dissociated gently to single cells with TrypLE. Single cells were then transferred in gelatin coated 384-well optical plates in StemPro 34 with 5 ng/nl FGF at a seeding density of 250,000 cells/cm$^2$. At this point cells were exposed to test compounds. At day 10, media with compound was removed and exchanged for a serum free media (SFM). T3, the thyroid hormone analog triiodothyronine, was added at day 10 to increase the red signal driven by the MYH6 promoter for more reliable imaging. Analysis of thyroid hormone effects on myosin heavy chain gene expression in cardiac and soleus muscles used a novel dot-blot mRNA assay. For RT-qPCR analysis T3 treatment was omitted to avoid interference with the biological mRNA expression of MYH6. Media was changed to PBS at day 14 and red fluorescence was imaged on an InCell 1000 high throughput microscope. For the quantification of cardiac induction, image analysis was done with the Cyteseer Image Analysis Software package by measuring the total area and intensity of the MYH6-mCherry reporter in each well. The MYH6-expression levels indicated in the graphs represent the multiplication of the total area and intensity of red fluorescence.

For toxicity assessment the hESC cell line was engineered for screening with a H2B-GFP reporter, allowing quantification of the cell number. Using Cyteseer, total GFP signal was quantified in each well. Wells with a GFP reduction of 20% or more (relative to vehicle only controls) were flagged for toxicity and were manually confirmed under a bright field microscope for evidence of cell death. Toxicity was consistent across replicates, and doses that caused toxicity were removed from the dataset displayed in the figures.

For the screens, Z scores (Z score=(average of treated–average of DMSO)/StDev of DMSO) were calculated using the fluorescence readout for each concentration normalized to DMSO treated wells. Integrated Z scores over all concentrations were calculated by adding the Z scores of the 3 concentrations tested. Table 2 reports Z scores at a compound concentration of 1250 nM. Higher concentrations showed some cell toxicity for some compounds.

Example 2

General Synthetic Procedures for Obtaining Compounds of Formula I

The norbornene-based compounds of general structure I:

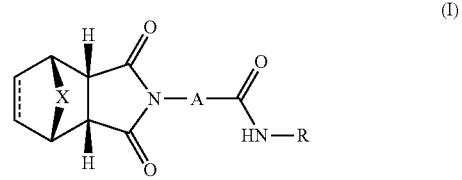

may be synthesized according to the following scheme 1:

Scheme 1: General Synthetic Procedure 1

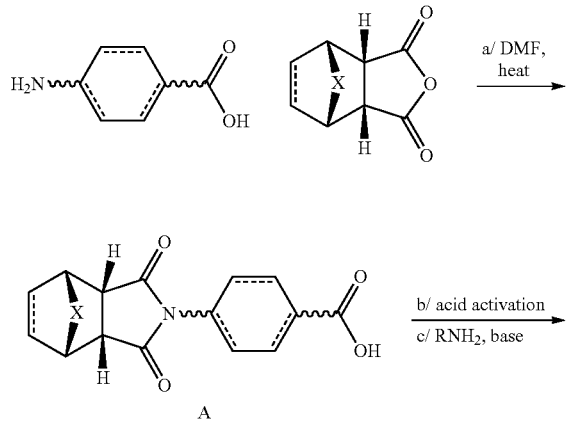

23

-continued

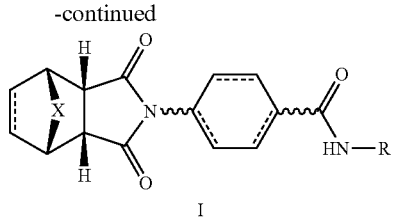

I

Compound A: Triethylamine (1.1 eq.) and the desired norbornene (1 eq.) was added to a solution of 4-amino acid (1 eq.) in DMF. The solution is heated overnight at 120° C. After return to room temperature, the solvent is evaporated. The residue is then dissolved in an organic solvent, washed and dried. The solution is concentrated to yield the desired intermediate A that is used as is or purified.

Compound of general formula I: Acid A was activated using conventional methods. For example, A can be treated with thionyl chloride. When conversion to the acid chloride was complete, excess thionyl chloride was removed and a solution of the appropriate amine and 1 eq. of a base such as pyridine or triethylamine in an inert solvent such as DCE or THF was added. The resulting solution was stirred overnight at temperatures ranging from room temperature to 70° C. and the crude product was purified.

Alternatively, compounds of general formula I can be prepared following Scheme 2

Scheme 2: General Synthetic Procedure 2

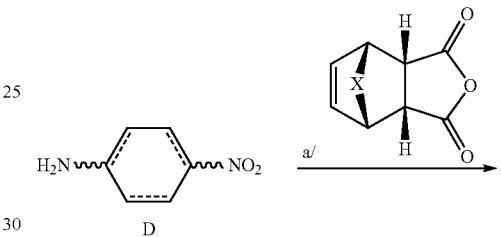

a/ activation of acid
b/ RNH2, base
c/ nitro reduction d/ DMF,

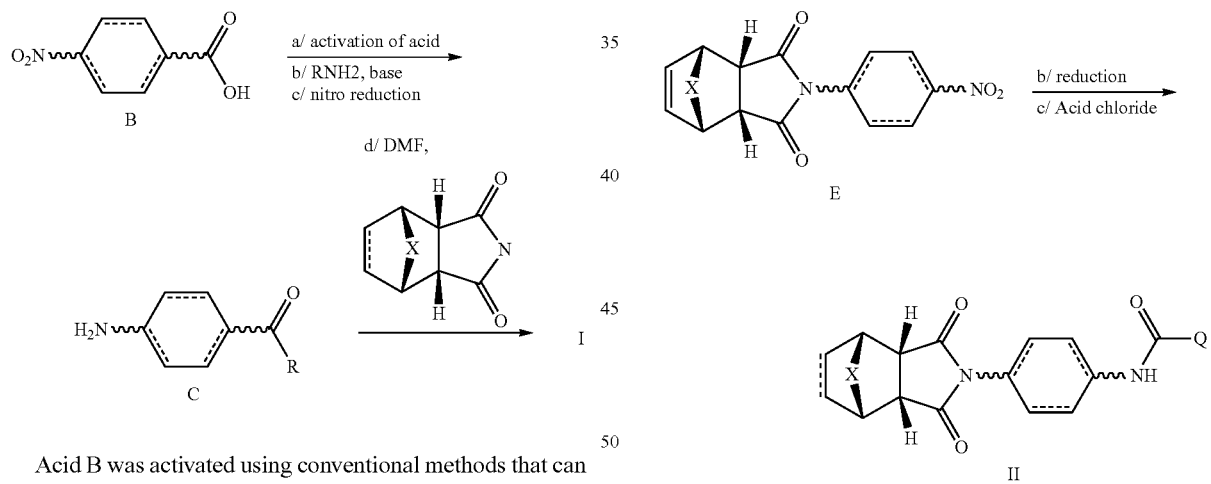

Acid B was activated using conventional methods that can be found in standard reference books. For example, B can be treated with thionyl chloride. When conversion to the acid chloride was complete, excess thionyl chloride was removed and a solution of the appropriate amine and 1 eq. of a base such as pyridine or triethylamine in an inert solvent such as DCE, THF was added. The mixture was stirred overnight at temperature ranging from room temperature to 70° C. and the crude material purified. The nitro intermediate was then reduced using conventional methods. For example, the reduction can be performed by hydrogenation in the presence of a catalyst or by chemical reduction with sodium dithionite. After conventional work up and purification, C is obtained.

Compound of general formula I is obtained by heating C with the desired norbornene using the procedure described for Compound A.

24

Example 3

General Synthetic Procedures for Obtaining Compounds of Formula II

The norbornene-based compounds of general structure II:

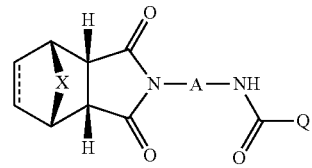

(II)

may be synthesized according to the following scheme 3:

Scheme 3: General Synthetic Procedure 3

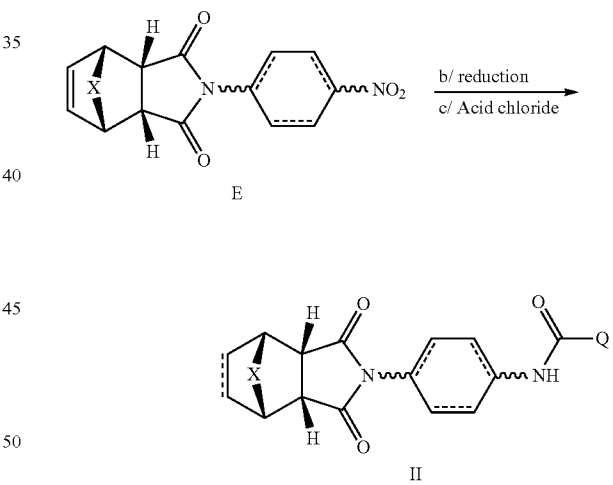

Scheme 3, step a: Compound of general formula II is obtained by heating D with the desired norbornene using the procedure described for Compound A.

Scheme 3, step b: The nitro intermediate E was reduced using conventional methods that can be found in standard reference books. For example, the reduction can be performed by hydrogenation in presence of a catalyst to reduce both the nitro function and the norbornene double bond if desired or by chemical reduction with sodium dithionite to selectively reduce the nitro function. After conventional work up and purification, the amine is treated with the desired activated acid using standard methods to produce compounds of general formula II.

Steps a and c can be performed in reversed order.

Example 4

Examples of Compounds of General Formula I and II

TABLE 1

Examples of Compounds of general formula I and II

| Cmpd # | Structure |
|---|---|
| 1 | (structure) |
| 2 | (structure) |
| 3 | (structure) |
| 4 | (structure) |
| 5 | (structure) |
| 6 | (structure) |
| 7 | (structure) |

TABLE 1-continued

Examples of Compounds of general formula I and II

| Cmpd # | Structure |
|---|---|
| 8 | (structure) |
| 9 | (structure) |
| 10 | (structure) |
| 11 | (structure) |
| 12 | (structure) |
| 13 | (structure) |
| 14 | (structure) |

TABLE 1-continued

Examples of Compounds of general formula I and II

| Cmpd # | Structure |
|---|---|
| 15 | 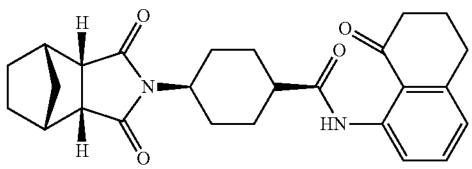 |
| 16 | 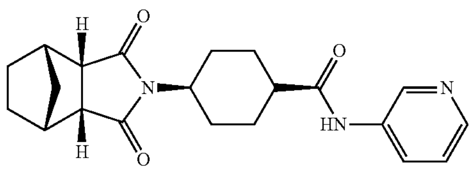 |
| 17 | 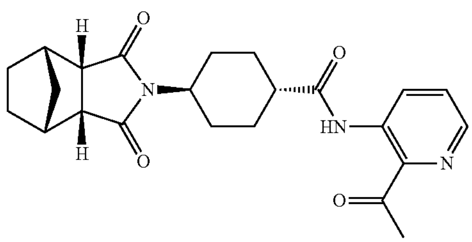 [SMILES: CC(=O)c1ncccc1NC(=O)[C@H]1CC[C@H](N2C(=O)[C@@H]3[C@@H]4CC[C@@H](C4)[C@@H]3C2=O)CC1] |
| 18 | 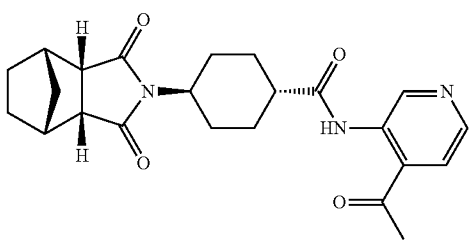 [SMILES: CC(=O)c1ccncc1NC(=O)[C@H]1CC[C@H](N2C(=O)[C@@H]3[C@@H]4CC[C@@H](C4)[C@@H]3C2=O)CC1] |
| 19 | 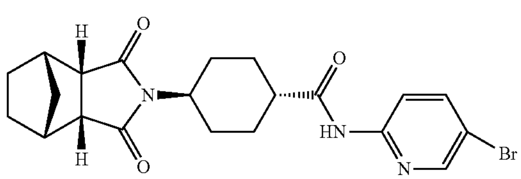 [SMILES: O=C1[C@@H]2[C@@H]3CC[C@@H](C3)[C@@H]2C(=O)N1[C@H]1CC[C@H](C(=O)Nc2ccc(Br)cn2)CC1] |
| 20 | 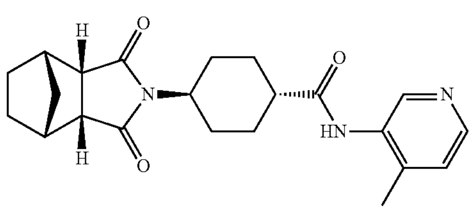 [SMILES: Cc1ccncc1NC(=O)[C@H]1CC[C@H](N2C(=O)[C@@H]3[C@@H]4CC[C@@H](C4)[C@@H]3C2=O)CC1] |
| 21 | 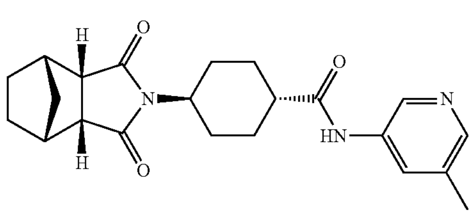 [SMILES: Cc1cncc(NC(=O)[C@H]2CC[C@H](N3C(=O)[C@@H]4[C@@H]5CC[C@@H](C5)[C@@H]4C3=O)CC2)c1] |
| 22 | 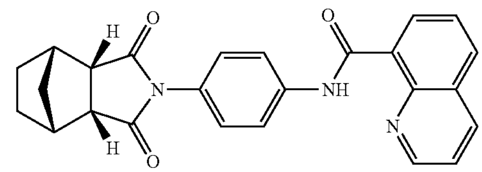 [SMILES: O=C(Nc1ccc(N2C(=O)[C@@H]3[C@@H]4CC[C@@H](C4)[C@@H]3C2=O)cc1)c1cccc2cccnc12] |

Example 5

Synthetic Procedures and Analytical Data

Scheme 1, Step a: Triethylamine (0.92 mL, 6.6 mmol) and the desired anhydride (6 mmol) were added to a solution of 4-amino acid (6 mmol) in 5 mL DMF. The solution was heated overnight at 120° C. After return to room temperature, the solvent was evaporated. The residue was then dissolved in ethyl acetate (100 mL) and washed with 1N HCl (20 mL). The organic layer was washed with brine (25 mL) and dried with anhydrous magnesium sulfate. The solution was filtered to yield the crude intermediate A. It was purified by liquid chromatography.

Compound A-1: 4-endo-dihydronorbornyl benzoic acid: (DCM/MeOH 9/1 Rf 0.5) beige solid (84% yield). $^1$H NMR (300 MHz, CD$_3$OD); 1.41 (d, J=8.4 Hz, 2H), 1.61-1.69 (m, 4H), 2.89 (bs, 2H), 3.26 (bs, 2H), 7.41 (d, J=8.7 Hz, 2H), 8.04 (s, OH), 8.19 (d, J=8.7 Hz, 2H).

Compound A-2: 4-(endo-dihydronorbornyl)-trans-cyclohexanecarboxylic acid: white solid (35% yield). DCM/MeOH 9/1 Rf 0.8; LC-MS (1000 (+)-5.5-254-80:20) Rt 3.49 min; 246.02 [M−COOH], 291.75 [M+1H]; $^1$H NMR (300 MHz, CDCl$_3$) 1.25 (d, J=8.4 Hz, 2H), 1.46-1.69 (m, 8H), 2.13 (d, J=11.7 Hz, 2H), 2.21-2.44 (m 3H), 2.74 (bs, 2H), 2.99 (bs, 2H), 3.98 (tt, J=12.1 and 3 Hz, 1H), 8.01 (s, OH).

Compound A-3: 4-(endo-dihydronorbornyl)-cis-cyclohexanecarboxylic acid: white solid (73% yield). Hex/EtOAc 1/1 Rf 0.4; LC-MS (1000 (+)-5.5-254-80:20) Rt 3.49 min; 246.02 [M−COOH], 291.75 [M+1H]; $^1$H NMR (300 MHz, CDCl$_3$): 1.23 (d, J=8.4 Hz, 2H), 1.46-1.62 (m, 8H), 2.28-2.45 (m, 5H), 2.71 (bs, 2H), 2.97 (bs, 2H), 3.96 (tt, J=12.1 and 3 Hz, 1H), 8.01 (s, 1H).

Compound A-4: 4-(endo-bicyclo[2,2,2]octane-2,3-imidyl)benzoic acid: off-white solid (99% yield). DCM/MeOH 9/1 Rf 0.2, LC-MS (1000 (+)-5.5-254-80:20) Rt 3.49 min; 246.02 [M−COOH], 291.75 [M+1H]; $^1$H NMR (300 MHz, DMSO) 1.46 (s, 4H), 1.63 (s, 4H), 2.05 (s, 2H), 2.50 (s, 2H), 7.41 (d, J=8.4 Hz, 2H), 8.05 (d, J=8.7 Hz, 2H), 13.15 (br s, 1 H).

Scheme 1, Steps b and c: 1 g of the appropriate Compound A was heated overnight in 5 mL thionyl chloride at 70° C. TLC (DCM/MeOH 9/1) showed complete conversion to the acid chloride. Excess thionyl chloride was removed to afford the acid chloride. The acid chloride was dissolved in 20 mL of DCE. 0.3 mL of the solution was added to 30 mg of the appropriate amine and 0.1 mL of pyridine. Solutions were heated at 50° C. overnight and the crude purified by liquid chromatography.

Scheme 2, steps a and b: 3 g (18 mmol) of 4-nitrobenzoic acid was dissolved in 10 mL of thionyl chloride. The mixture was heated at reflux for 2 hours. The mixture was then cooled and the excess thionyl chloride was evaporated. The result was a light yellow solid used without purification in the next step. 1.2 equivalent of the desired amine RNH2 was added in 50 mL pyridine. The mixture was heated at reflux for 3-4 hours, cooled and the pyridine was evaporated. The residue was dissolved in ethyl acetate and washed with citric acid (10% in water) once, and with brine solution once. The organic layer was then dried with $Na_2SO_4$. The solvent was evaporated and the crude product purified by liquid chromatography.

1H]; 97.8% at 254 nM; $^1$H NMR (CDCl$_3$): 6.77 (d, J=8.4 Hz, 1H), 7.45-7.64 (m, 5H), 7.93 (d, J=8.4 Hz, 2H), 8.85 (dd, J=4.2 and 1.8 Hz, 1H), 8.92 (dd, J=7.5 and 1.5 Hz, 1H), 10.63 (NH).

Scheme 2, step d: 0.083 mmol of the desired anhydride was added to 0.083 mmol of intermediate prepared in Scheme 2 step b and 76 uL TEA in 1 mL DMF. The mixtures were heated overnight at 120° C. Solvent was evaporated and the residue dissolved in ethyl acetate. The organic layer was washed once with brine, dried with $Na_2SO_4$ and purified by liquid chromatography. Compounds of general formula I were obtained.

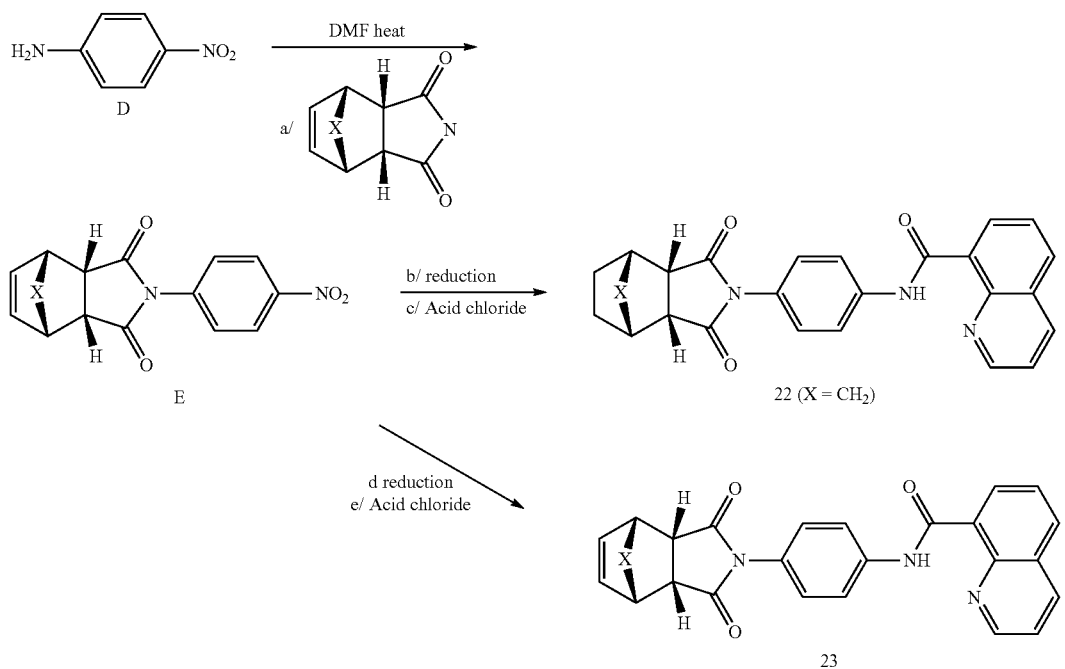

Scheme 3: Scheme for the synthesis of compounds of general formula II.

N-(2-methoxyphenyl)-4-nitrobenzamide: DCM 100%, Rf 0.8; yellow solid, 81% yield; LC-MS (1000 (+)-5.5-254-80: 20) Rt 3.85 min; 272.82 [M+1H]; 99.8% at 254 nM. $^1$H NMR (CDCl$_3$): 3.95 (s, 3H), 6.95 (dd, J=8.1 and 1.5 Hz, 1H), 7.04 (td, J=7.8 and 1.2 Hz, 1H), 7.14 (td, J=7.8 and 1.8 Hz, 1H), 8.05 (d, J=9 Hz, 2H), 8.35(d, J=9 Hz, 2H), 8.49 (d, J=4.1 Hz, 1H), 8.57 (bs, NH).

Scheme 2, step c: Compound C-1: N-(2-methoxyphenyl)-4-aminobenzamide: 3.96 g (0.016 mol) of N-(2-methoxyphenyl)-4-nitrobenzamide was dissolved in 200 mL of ethanol. Catalytic amount of palladium on carbon was added to the solution. The flask was purged with hydrogen twice and stirred under a hydrogen atmosphere overnight at room temperature. TLC (Hex/EtOAc, 1:1) confirmed that the reduction was complete. The catalyst was removed by paper filtration and the mixture was evaporated to afford 3.18 g (73% yield) of a tan/orange solid. LC-MS (1000 (+)-5.5-254-80:20) Rt 3.07 min; 243.02 [M+1H]; 100% at 254 nM.

Compound C-1: 4-amino-N-(quinolin-8-yl)benzamide: using the procedure described above in THF instead of ethanol. The amine was obtained as a yellow solid (49% yield). LC-MS (1000 (+)-5.5-254-80:20) Rt 2.89 min; 264.08[M+

Scheme 3, step a: Compound E (X=CH$_2$): Using the procedure described for compound A and starting from 1.64 g carbic anhydride (10 mmol), 1.67 mL triethylamine and 1.52 g 4-nitroaniline D, E was isolated as a yellow solid with 52% yield (DCM/MeOH, 9/1; Rf 0.6). LC-MS (1000 (+)-5.5-254-80:20): Rt 3.35 min, 96.8% at 254 nm. $^1$H NMR (300 MHz, CDCl$_3$): 1.62-1.68 (m, 1H), 1.80-1.86 (m, 1H), 3.49 (dd, J=1.63, 3.09 Hz, 2H), 3.55 (m$_e$, 2H), 6.27 (br t, J=1.80 Hz, 2H), 7.40-7.44 (m, 2H), 8.26-8.31 (m, 2H).

Scheme 3, Step b: N-(4-Aminophenyl)-(3aR,4S,7R,7aS)-1,3,3a,4,7,7a-hexahydro-1,3-dioxo-4,7-methano-2H-isoindol: 300 mg of the nitro precursor E were dissolved in 30 mL of EtOH and 40 mg of Pd/C (10%) added. The mixture was stirred at room temperature overnight under a hydrogen atmosphere. The solution was filtered through a pad of Celite, concentrated by rotavap. The crude product was purified by flash chromatography (Hex/EtOAc 1/1 Rf 0.2) to afford 180 mg (67% yield).

LC-MS (1000 (+)-10.0-254-80:20): Rt 3.14 min, 257 [M+H]$^+$ 98.8% at 254 nM. $^1$H NMR (300 MHz, CDCl$_3$): 1.43-1.72 (m, 6H), 2.85 (m, 2H), 3.21 (m, 2H), 3.81 (br s, 2H, NH$_2$), 6.71-6.75 (m, 2H), 6.98-7.01 (m, 2H).

Scheme 3, Step c: N-[4-((3aR,4S,7R,7aS)-1,3,3a,4,7,7a-hexahydro-1,3-dioxo-4,7-methano-2H-isoindol-2-yl)phenyl]-quinoline-8-carboxamide (22): Quinoline-8-carbonyl chloride was freshly prepared by heating 135 mg (0.78 mmol) of quinoline-8-carboxylic acid in an excess of thionyl chloride (622 µL) for three hours at 60-70° C. This mixture was added dropwise to a solution of 100 mg of the aniline precursor from step b (0.39 mmol) and 5 equivalents of triethylamine (1.95 mmol) in 7 mL of dry MeCN. The reaction mixture was stirred at room temperature for three days, concentrated in a vacuum and purified by flash chromatography (toluene/EtOAc/acetone 6/3/1 Rf 0.5). The product was obtained as an off-white solid with 87% yield (140 mg). LC-MS (1000 (+)-5.5-254-80:20): Rt 3.45 min, 412 [M+H]$^+$ >99% at 254 nM; $^1$H NMR (300 MHz, CDCl$_3$): 1.48-1.75 (m, 6H), 2.88 (m$_e$, 2H), 3.25 (m$_e$, 2H), 7.27-7.32 (m, 2H), 7.56 (dd, J=4.3, 8.3 Hz, 1H), 7.74 (dd, J=7.45, 7.50 Hz, 1H), 7.98-8.03 (m, 2H), 8.02 (br d, J=1.6 Hz, 1H), 8.34 (dd, J=1.8, 8.4 Hz, 1H), 8.96 (dd, J=1.6, 7.4 Hz, 1H), 9.01 (dd, J=1.8, 4.3 Hz, 1H).

Scheme 3, Step d: N-(4-Aminophenyl)-(3aR,4S,7R,7aS)-1,3,3a,4,7,7a-tetrahydro-1,3-dioxo-4,7-methano-2H-isoindol: 300 mg of E was dissolved in 20 mL THF. 5 mmol (5 eq.) of sodium dithionate and 5 mmol of potassium carbonate in 10 ml of water were added in one portion. After one hour at room temperature, brine was added. The product was extracted with ethyl acetate. The organic layers were combined, dried and concentrated. The crude product was purified by liquid chromatography (DCM/MeOH) to give 128 mg of the product.

Scheme 3, Step e: Using the procedure described in Scheme 3, step c and starting from compound described above, the desired compounds were obtained.

Example 6

Analytical Data for Compounds 1-22

Analytical data for compounds 1-22: Synthetic products were isolated using flash column chromatography with UV detection at 254 nm or PTLC with UV indicator. $^1$H NMR spectra were recorded at 300 MHz on a Varian Mercury 300. Chemical shifts were reported as ppm ( ) relative to the solvent (CDCl$_3$ at 7.26 ppm, CD$_3$OD at 3.31 ppm, d$_6$-DMSO at 2.50 ppm and 3.52 ppm). Low resolution mass spectra were obtained using Hitachi M-8000 mass spectrometer with an ESI source.

Purity of products was determined by HPLC using reverse phase chromatography (C18 column, 50×4.6 mm, 5 µm). Compounds were eluted using a gradient elution of 95/5 to 5/95 A/B over 5 min at a flow rate of 1.5 mL/min, where solvent A was aqueous 0.05% TFA and solvent B was acetonitrile (0.05% TFA). For purity data, peak area percent for the TIC, at 254 nm and retention time (t$_R$ in minutes) are provided.

1: white solid; 32% yield; DCM/MeOH 9/1 Rf 0.8; LC-MS (1000 (+)-5.5-254-80:20) Rt 2.46 min; 367.88 [M+1H] 97.9% at 254 nM; $^1$H NMR (300 MHz, CDCl$_3$+1 drop CD$_3$OD) 1.28 (d, J=8.4 Hz, 2H), 1.53-1.64 (m, 4H), 1.71-1.85 (m, 4H), 1.86 (bd, J=12.3 Hz, 2H), 2.12-2.38 (m, 3H), 2.76 (bs, 2H), 3.01 (bs, 2H), 4.08 (tt, J=12.3 and 3.9 Hz, 1H), 7.21 (dd, J=8.4 and 3.6 Hz, 1H), 8.14 (bd, J=3.6 Hz, 1H), 8.20 (bd, J=8.4 Hz, 1H), 8.42 (d, J=2.1 Hz, 1H).

2: yellow solid; 8% yield; DCM/MeOH 9/1 Rf 0.7; LC-MS (1000 (+)-5.5-254-80:20) Rt 1.68 min; 367.89 [M+1H] 97.3% at 254 nM; $^1$H NMR (300 MHz, CDCl$_3$) 1.25 (d, J=8.4 Hz, 2H), 1.46-1.75 (m, 8H), 2.07 (bd, J=12.3 Hz, 2H), 2.23-2.37 (m, 3H), 2.75 (bs, 2H), 3.02 (bs, 2H), 4.08 (tt, J=12.3 and 3.9 Hz, 1H), 7.31 (bs, NH), 7.48 (d, J=6.3 Hz, 2H), 8.50 (bd, J=6.3 Hz, 2H).

3: brown solid; 38% yield; Hex/EtOAc 1/1 Rf: 0.4; LC-MS (1000 (+)-5.5-254-80:20) Rt 4.40 min; 408.28 [M+1H] 94.7% at 254 nM; $^1$H NMR (300 MHz, CDCl$_3$) 1.26 (d, J=8.4 Hz, 2H), 1.53-1.85 (m, 6H), 2.16 (bd, J=12.3 Hz, 2H), 2.28-2.49 (m, 3H), 2.67 (s, 3H), 2.75 (bs, 2H), 3.01 (bs, 2H), 4.08 (tt, J=12.3 and 3.9 Hz, 1H), 7.11 (t, J=7.5 Hz, 1H), 7.55 (t, J=8.7 and 1.5 Hz, 1H), 7.90 (dd, J=7.8 and 1.2 Hz, 1H), 8.76 (d, J=8.4 Hz, 1H), 11.84 (s, NH).

4: off white solid; 6% yield; DCM/MeOH 9/1 Rf 0.7; LC-MS (1000 (+)-5.5-254-80:20) Rt 1.27 min; 367.88 [M+1H] 97.5% at 254 nM; $^1$H NMR (300 MHz, CDCl$_3$) 1.26 (d, J=8.4 Hz, 2H), 1.51-1.74 (m, 9H), 2.09 (bd, J=11.7 Hz, 2H), 2.26-2.39 (m, 2H), 2.75 (bs, 2H), 3.01 (bs, 2H), 4.01-4.17 (m, 1H), 7.01-7.05 (m, 1H), 7.69 (dt, J=9 and 2.1 Hz, 1H), 7.99 (bs, NH), 8.21 (d, J=8.7 Hz, 1H), 8.24-8.27 (m, 1H).

5: (DCM/MeOH, 9/1; Rf 0.4) pinkish solid, 30% yield; LC-MS (1000 (+)-5.5-254-80:20) Rt 2.64 min; 397.88 [M+1H] 99.6% at 254 nM $^1$H NMR (300 MHz, CDCl$_3$+CD$_3$OD) 1.17 (d, J=8.4 Hz, 2H), 1.47-1.74 (m, 6H), 1.96 (bd, J=11.7 Hz, 2H), 2.12-2.34 (m, 3H), 2.68 (bs, 2H), 2.96 (bs, 2H), 3.83 (s, 3H), 4.04 (t, J=12.6 Hz, 1H), 6.65 (dd, J=9 and 0.6 Hz, 1H), 7.96 (dd, J=9 and 2.7 Hz, 1H), 8.07 (d, J=2.7 Hz, 1H).

6: (DCM/MeOH, 9/1, Rf 0.3) transparent film, 45% yield; LC-MS (1000 (+)-5.5-254-80:20) Rt 1.39 min; 398.00 [M+1H] 97.2% at 254 nM; $^1$H NMR (300 MHz, CDCl$_3$) 1.24 (d, J=8.4 Hz, 2H), 1.44-1.74 (m, 6H), 2.18 (bd, J=11.7 Hz, 2H), 2.26-2.48 (m, 3H), 2.51(s, 3H), 2.73 (bs, 2H), 3.00 (bs, 2H), 3.81 (s, 3H), 3.92-4.02 (m, 1H), 7.14 (d, J=8.4 Hz, 1H), 7.87 (bs, NH), 8.25 (dd, J=8.7 and 2.1 Hz, 1H), 8.51 (d, J=2.7 Hz, 1H).

7: pale yellow solid; 35% yield; DCM/MeOH, 9/1 Rf 0.6; LC-MS (1000 (+)-5.5-254-80:20) Rt 2.91 min; 401.68 [M+1H] 98.7% at 254 nM; $^1$H NMR (300 MHz, CDCl$_3$) 1.26 (d, J=8.4 Hz, 2H), 1.51-1.74 (m, 6H), 2.18 (bd, J=11.7 Hz, 2H), 2.26-2.48 (m, 3H), 2.73 (bs, 2H), 3.00 (bs, 2H), 3.92-4.02 (m, 1H), 7.25 (dd, J=8.4 and 4.9 Hz, 1H), 7.69 (bs, NH), 8.10 (dd, J=4.9 and 1.8 Hz, 1H), 8.73 (dd, J=8.4 and 1.8 Hz, 1H).

8: (DCM/MeOH, 9/1, Rf 0.5) white solid, 40% yield; LC-MS (1000 (+)-5.5-254-80:20) Rt 3.23 min; 435.75 [M+1H] 96.2% at 254 nM; $^1$H NMR (300 MHz, CDCl$_3$+CD$_3$OD) 1.46 (d, J=8.4 Hz, 2H), 1.47-1.68 (m, 6H), 1.95 (bd, J=11.7 Hz, 2H), 2.16-2.38 (m, 3H), 2.67 (bs, 2H), 2.98 (bs, 2H), 3.92-4.02 (m, 1H), 7.56 (d, J=9 Hz, 1H), 8.45 (dd, J=9 and 2.4 Hz, 1H), 8.52 (d, J=2.4 Hz, 1H).

9: (DCM/MeOH, 95/5, Rf 0.2) pale yellow solid, 10% yield. $^1$H NMR (300 MHz, CDCl$_3$) 1.46 (d, J=8.4 Hz, 2H), 1.47-1.68 (m, 6H), 1.95 (bd, J=11.7 Hz, 2H), 2.16-2.38 (m, 3H), 2.67 (bs, 2H), 2.98 (bs, 2H), 3.92-4.02 (m, 1H), 7.36 (d, J=1.8 Hz, 1H), 7.65 (d, J=1.8 Hz, 1H), 8.25 (d, J=5.4 Hz, 1H).

10: white solid; 58% yield; DCM/MeOH 95/5 Rf 0.8; LC-MS (1000 (+)-5.5-254-80:20) Rt 3.58 min; 418 [M+1H] 92.4% at 254 nM; $^1$H NMR (300 MHz, CDCl$_3$) 1.24 (d, J=8.4 Hz, 2H), 1.51-1.72 (m, 4H), 2.14 (bd, J=11.7 Hz, 2H), 2.26-2.41 (m, 3H), 2.73 (bs,2H), 2.99 (bs, 2H), 3.91 (s, 3H), 4.03 (t, J=12.6 Hz, 1H), 7.05 (t, J=7.8 Hz, 1H), 7.51 (t, J=8.7 Hz, 1H), 8 (dd, J=7.8 and 1.2 Hz, 1H), 8.71 (d, J=8.7 Hz, 1H), 11.15 (bs, 1H).

11: yellow solid; 46% yield; DCM/MeOH 95/5 Rf 0.7; LC-MS (1000 (+)-5.5-254-80:20) Rt 4.38 min; 469 [M+1H] 99.4% at 254 nM; $^1$H NMR (300 MHz, CDCl$_3$) 1.26 (d, J=8.4 Hz, 2H), 1.47-1.74 (m, 8H), 2.18 (bd, J=11.7 Hz, 2H), 2.26-2.48 (m, 3H), 2.75 (bs, 2H), 3.00 (bs, 2H), 4.04 (t, J=12.6 Hz, 1H), 7.15 (t, J=7.2 Hz, 1H), 7.25-7.31 (m, 1H), 7.38-7.47 (m, 3H), 7.58 (d, J=7.5 Hz, 1H), 8.34 (d, J=8.1 Hz, 1H), 10.17 (bs, NH).

12: beige solid, 40% yield, Hex/EtOAc 1/1 Rf 0.5, $^1$H NMR (300 MHz, CDCl$_3$) 1.24 (d, J=8.4 Hz, 2H), 1.48-1.79 (m, 7H), 2.29-2.46 (m, 5H), 2.64 (s, 3H), 2.72 (bs, 2H), 2.98 (bs, 2H), 3.97-4.08 (m, 1H), 7.07-7.13 (m, 1H), 7.54 (tt, J=8.7 and 1.5 Hz, 1H), 7.89 (td, J=8.1 and 1.5 Hz, 1H), 8.76+8.87 (dd, J=8.7 and 0.9 Hz, 1H), 11.80+11.96 (bs, NH).

13: (DCM/MeOH, 9/1; Rf 0.7) beige solid, 21% yield ; LC-MS (1000 (+)-5.5-254-80:20) Rt 1.47 min; 383.88 [M+1H] 97.2% at 254 nM; $^1$H NMR (300 MHz, CDCl$_3$+ CD$_3$OD) 1.06 (d, J=8.4 Hz, 2H), 1.39-1.59 (m, 6H), 1.82 (bd, J=11.7 Hz, 2H), 2.06-2.38 (m, 3H), 2.58 (bs, 2H), 2.88 (bs, 2H), 4.04 (t, J=12.6 Hz, 1H), 7.59 (s, 1H), 7.65 (s, 1H), 7.87 (s, 1H).

14: brown oil; 51% yield; Hex/EtOAc 1/1 Rf 0.6; LC-MS (1000 (+)-5.5-254-80:20) Rt 3.73 min; 434.48 [M+1H] 97.5% at 254 nM; $^1$H NMR (300 MHz, CDCl$_3$) 1.21 (d, J=8.4 Hz, 2H), 1.53-1.67 (m, 8H), 2.07-2.15 (m, 4H), 2.19-2.54 (m, 3H), 2.61-2.78 (m, 4H), 2.88-3.-02 (m, 4H), 3.98-4.14 (m, 1H), 6.91 (dd, J=7.5 and 1.5 Hz, 1H), 7.42 (t, J=7.5 Hz, 1H), 8.60 (dd, J=7.5 and 1.5 Hz, 1H), 12.23 (bs, 1H).

15: off-white solid; 11% yield, Hex/EtOAc 1/1 Rf 0.8; $^1$H NMR (300 MHz, CDCl$_3$) 1.24-1.26 (m, 2H), 1.48-1.72 (m, 10H), 2.07-2.15 (m, 1H), 2.29-2.48 (m, 3H), 2.66-2.74 (m, 2H), 2.95-3.03 (m, 2H), 3.94-4.05 (m, 1H), 6.91 (t, J=5.6 Hz, 1H), 7.43 (dt, J=6.3 and 2.6 Hz, 1H), 8.61+8.72 (d, J=6.7 Hz, 1H), 12.23+12.37 (bs, NH).

16: off-white solid; 23% yield, DCM/MeOH 9/1 Rf 0.8; LC-MS (1000 (+)-5.5-254-80:20) Rt 2.58 min; 367.75 [M+1H]; 97.7% at 254 nM.

17: off-white solid; 17% yield, DCM/MeOH 9/1 Rf 0.8; LC-MS (1000 (+)-5.5-254-80:20) Rt 4.35 min; 409.28 [M+1H]; $^1$H NMR (300 MHz, CDCl$_3$) 1.24 (d, J=8.4 Hz, 2H), 1.49 (s, 9H), 1.46-1.69 (m, 4H), 2.13 (d, J=11.7 Hz, 2H), 2.22-2.89 (m, 3H), 2.79 (bs, 2H), 2.80 (s, 3H), 2.99 (bs, 2H), 3.98 (tt, J=12.1 and 3 Hz, 1H), 7.43-7.47 (m, 1H), 7.35 (d, J=4.40 and 0.3 Hz, 1H), 9.09 (d, J=8.53 and 0.3 Hz, 1H), 11.62 (s, NH).

18: off-white solid; 16% yield, DCM/MeOH 9/1 Rf 0.7; LC-MS (1000 (+)-5.5-254-80:20) Rt 3.46 min; 409.48 [M+1H], $^1$H NMR (300 MHz, CDCl$_3$) 1.24 (d, J=8.4 Hz, 2H), 1.49 (s, 9H), 1.46-1.69 (m, 4H), 2.13 (d, J=11.7 Hz, 2H), 2.22-2.89 (m, 3H), 2.71 (s, 3H), 2.79 (bs, 2H), 2.99 (bs, 2H), 3.98 (tt, J=12.1 and 3 Hz, 1H), 7.64 (d, J=5.23 Hz, 1H), 8.47 (d, J=5.53 Hz, 1H), 10.05 (s, 1H), 11.20 (s, NH).

19: white solid, 5% yield, Hex/EtOAc, 1/1, Rf: 0.5; LC-MS (1000 (+)-5.5-254-80:20) Rt 4.00 min; 448 [M+1H]; $^1$H NMR (300 MHz, CDCl$_3$) 1.28 (d, J=8.4 Hz, 2H), 1.53-1.64 (m, 4H), 1.71-1.85 (m, 4H), 2.22 (bd, J=12.3 Hz, 2H), 2.42 (dq, J=12.6 and 3.6 Hz, 2H), 2.56 (tt, J=12 and 3.3 Hz, 1H), 2.76 (bs,2H), 3.01 (bs, 2H), 4.08 (tt, J=12.3 and 3.9 Hz, 1H), 7.79 (dd, J=8.8 and 2.5 Hz, 1H), 7.86 (bs, 1H), 8.16 (d, J=8.8 Hz, 1H), 8.30 (d, J=2.5 Hz, 1H).

20: transparent film, 46% yield, DCM/MeOH 95/5 Rf 0.3; $^1$H NMR (300 MHz, CDCl$_3$) 1.24 (d, J=8.4 Hz, 2H), 1.46-1.69 (m, 8H), 2.13 (d, J=11.7 Hz, 2H), 2.25 (s, 3H), 2.22-2.89 (m, 3H), 2.74 (bs, 2H), 2.99 (bs, 2H), 3.98 (tt, J=12.1 and 3 Hz, 1H), 7.02 (d, J=4.8 Hz, 1H), 7.56 (bs, NH), 8.09 (d, J=4.8 Hz, 1H), 8.76 (s, 1H).

21: yellow solid, 32% yield, DCM/MeOH 95/5 Rf 0.3; $^1$H NMR (300 MHz, CDCl$_3$) 1.24 (d, J=8.4 Hz, 2H), 1.46-1.69 (m, 4H), 2.13 (d, J=11.7 Hz, 2H), 2.32 (s, 3H), 2.22-2.89 (m, 3H), 2.74 (bs, 2H), 2.99 (bs, 2H), 3.98 (tt, J=12.1 and 3 Hz, 1H), 8.15 (s, 1H), 8.30 (s, 1H), 8.35 (s, 1H).

22: off-white solid, 87% yield, toluene/EtOAc/acetone, 6/3/1 Rf 0.5; $^1$H NMR (300 MHz, CDCl$_3$): 1.48-1.75 (m, 6H), 2.88 (m$_e$, 2H), 3.25 (m$_e$, 2H), 7.27-7.32 (m, 2H), 7.56 (dd, J=4.3, 8.3 Hz, 1H), 7.74 (dd, J=7.45, 7.50 Hz, 1H), 7.98-8.03 (m, 2H), 8.02 (br d, J=1.6 Hz, 1H), 8.34 (dd, J=1.8, 8.4 Hz, 1H), 8.96 (dd, J=1.6, 7.4 Hz, 1H), 9.01 (dd, J=1.8, 4.3 Hz, 1H).

Example 7

Potency of Compounds of General Structures I and II

The potency of several compounds of structures I and II using the above-described testing methods is reported in Table 2. Table 2 provides the potency of some of the compounds in the Wnt assay and in the human cardiomyocyte screening assay.

TABLE 2

Summary of Wnt inhibition and cardiogenesis for compounds of general formula I and II

| Compound Number | Wnt Assay % inh. @ 1000 nM | Wnt Assay IC$_{50}$ (nM) | Cardiogenesis Assay Z score[b] vs DMSO @ 1250 nM |
|---|---|---|---|
| DMSO | 0 | | 0 |
| 1 | 89 ± 1 | 42 | 0.6 |
| 2 | 84 ± 1 | 47 | 0.2 |
| 3 | 91 ± 1 | 14 | 132.9 |
| 4 | 82 ± 5 | 86 | 1.8 |
| 5 | 75 ± 2 | 344 | NM |
| 6 | 48 ± 7 | 1380 | NM |
| 7 | 13 ± 1 | 166 | 3.1 |
| 8 | 46 ± 7 | 870 | NM |
| 9 | 68 ± 4 | 374 | NM |
| 10 | 86 ± 1.6 | 67 | 44.9 |
| 11 | 88 ± 2 | 193 | 42.7 |
| 12 | 91 ± 1 | 23 | 117.0 |
| 13 | 86 ± 2 | 152 | 99.2 |
| 14 | 92 ± 1.3 | 19 | 69.6 |
| 17 | NM[a] | 2 | 236.2 |
| 18 | NM | 287 | 0.2 |
| 19 | 68 ± 4 | NM | NM |
| 20 | 0 | NM | NM |
| 21 | 49 ± 5 | NM | NM |
| 22 | 91 ± 1 | 96 | 0.9 |

[a]NM, not measured;
[b]Z scores (Z score = (average of treated − average of DMSO)/StDev of DMSO) were calculated using the fluorescence readout at a compound concentration of 1250 nM normalized to DMSO treated wells. Integrated Z scores over all concentrations were calculated by adding the Z scores of the 3 concentrations tested. Any compound with an integrated Z score higher than 6 fold was assumed a hit.

Example 8

Study of Small Molecule Inducers of Stem Cell Cardiogenesis

A human embryonic stem cell (mESC)-based high throughput assay used to screen a commercially available and diverse small molecule library of 550 known pathway modulators (InhibitorSelect and StemSelect) to identify small molecules that stimulate cardiomyocyte differentiation. The assay was developed to probe compounds that acted between 2 and 6 days of differentiation in monolayer culture, corresponding to the time window when the ESCs become specified to follow the cardiomyocyte lineage. The assay readout is eGFP expression from the cardiomyocyte-specific alpha myosin heavy chain (aMHC) gene. eGFP fluorescence is imaged by high throughput microscopy and quantified by calculating the integrated fluorescence intensity within intensity thresholded mask of areas of cardiomyocyte differentiation. About 30,000 data points were screened encompassing ~14,000 unique small molecules, each tested at 1 and 5 µg/mL doses. After data analysis and filtration of artifacts using statistics and visual confirmation in images, one compound had a strong cardiogenic potential as described below.

A biological time course experiment showed the biological action of each molecule is maximized at overlapping but non-identical developmental windows between days 2 to 5 of mESC to cardiomyocyte differentiation. Early analysis of molecular markers induced in secondary assays suggest that these compounds act by regulating mesoderm and endodermal patterning, consistent with the time frame when they are active. An SAR effort is undertaken to investigate the structure-activity relationship (SAR) of the "hit" molecule with the goal of identifying an optimized structure yielding maximum biological potency; and molecular space amenable to affinity ligand linkage without abrogating biological activity. The medicinal chemistry and SAR studies for the molecules of general structures I and II were described above.

The molecules would be expected to be used for stimulating differentiation of stem cells, in particular but not limited to ESCs and IPSCs to endoderm (e.g., liver, lung and pancreas) and cardiac derivatives.

Tissue recombination assays were used leading to the identification of non-cardiac mesoderm and endoderm as sources of heart-inducing factors.

Although the disclosure has been described with reference to the above examples, it will be understood that modifications and variations are encompassed within the spirit and scope of the disclosure. Accordingly, the disclosure is limited only by the following claims.

What is claimed is:

1. A compound of Formula I:

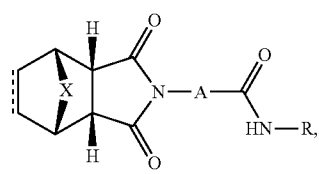

(I)

or a pharmaceutically acceptable salt thereof, wherein:
A is cis-cyclohexyl or trans-cyclohexyl substituted in a 1,4-pattern and optionally substituted;
X is $CH_2$, $CH_2$—$CH_2$ or oxygen;
R is one of:

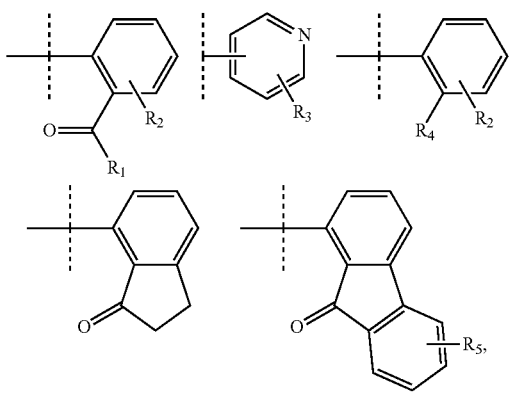

wherein
$R_1$ is a $C_{1-4}$ alkyl, $C_{1-4}$ alkoxy, substituted $C_{1-4}$ alkyl, substituted $C_{1-4}$ alkoxy, $C_{1-4}$ alkyl amine, $C_{2-6}$ cyclic amine, aryl or heteroaryl;
$R_2$ is hydrogen, $C_{1-4}$ alkyl, $C_{1-4}$ alkoxy, substituted $C_{1-4}$ alkyl, substituted $C_{1-4}$ alkoxy, $C_{1-4}$ alkyl amine, heteroalkyl, halogen or fluorinated alkyl;
$R_3$ is selected from the group consisting of hydrogen, halogen, $C_{1-4}$ alkyl, $C_{1-4}$ alkoxy, substituted $C_{1-4}$ alkyl, substituted $C_{1-4}$ alkoxy, hydroxyl, trifluoromethyl, acyl-$C_{1-4}$ alkyl, $C_{1-4}$ alkyl amine, $C_{2-6}$ cyclic amine, $C_{1-4}$ ester, $C_{1-4}$ amide and heteroaryl;
$R_4$ is a heteroaryl such as but not limited to furan, oxazole or pyrazole;
$R_5$ is a hydrogen, halogen, $C_{1-4\ alkyl}$, $C_{1-4}$ alkoxy, substituted $C_{1-4}$ alkyl or substituted $C_{1-4}$ alkoxy,
or $R_1$ and $R_2$ together with their intervening carbons comprise a ring system; and
is either a double or a single bond.

2. The compound of Formula I of claim 1, having formula:

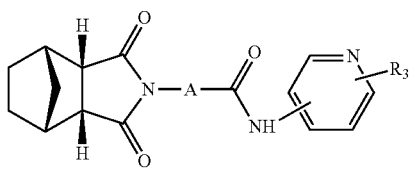

$R_3$ is selected from the group consisting of hydrogen, halogen, $C_{1-4}$ alkyl, $C_{1-4}$ alkoxy, substituted $C_{1-4}$ alkyl, substituted $C_{1-4}$ alkoxy, hydroxyl, trifluoromethyl, acyl-$C_{1-4}$ alkyl, $C_{1-4}$ alkyl amine, $C_{2-6}$ cyclic amine, $C_{1-4}$ ester and $C_{1-4}$ amide.

3. The compound of Formula I of claim 1, having formula:

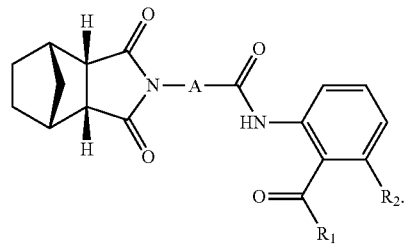

4. The compound of Formula I of claim 1, having formula:

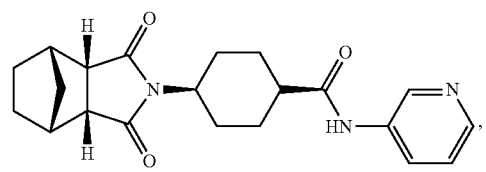

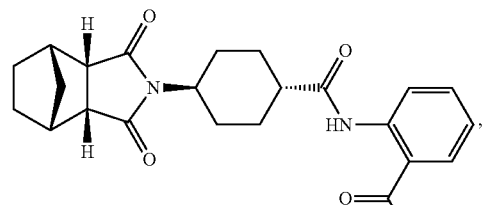

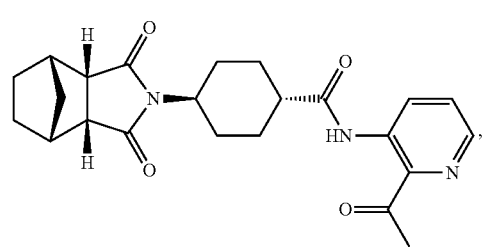

-continued
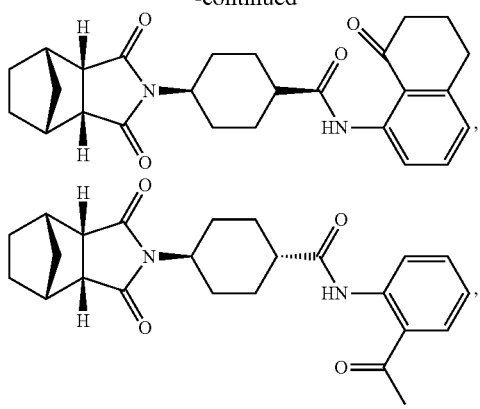
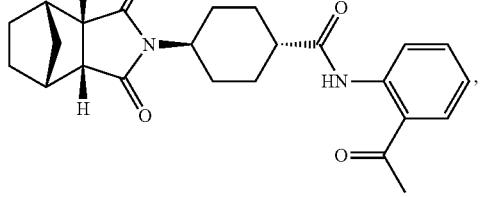
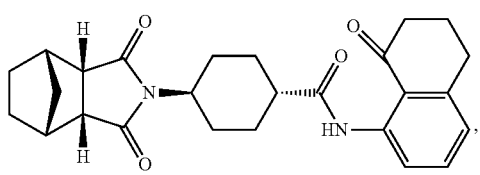
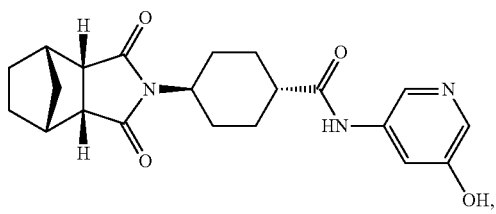
-continued
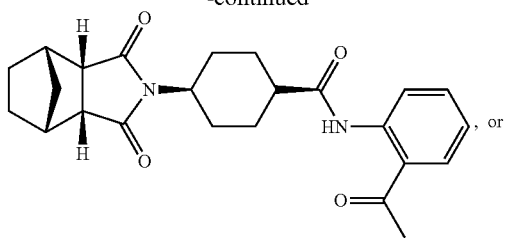
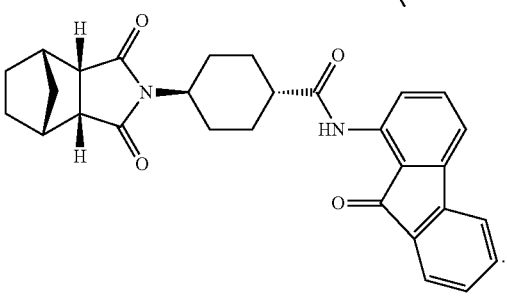
5. The compound of claim 1 wherein the compound is
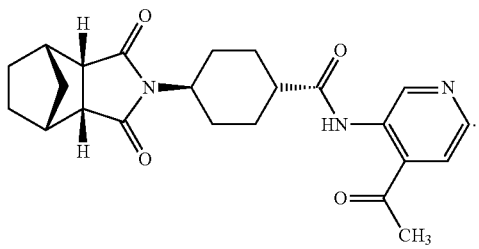
* * * * *